United States Patent
Sainani et al.

(10) Patent No.: US 8,927,753 B2
(45) Date of Patent: Jan. 6, 2015

(54) METHOD FOR PREPARING DI-ORGANO-DIALKOXYSILANES

(71) Applicant: Saudi Basic Industries Corporation, Riyadh (SA)

(72) Inventors: Jaiprakash Brijlal Sainani, Savli (IN); Vimalkumar Mahendrabhai Patel, Savli (IN); Mahesh Davadra, Savli (IN)

(73) Assignee: Saudi Basic Industries Corporation, Riyadh (SA)

( * ) Notice: Subject to any disclaimer, the term of this patent is extended or adjusted under 35 U.S.C. 154(b) by 143 days.

(21) Appl. No.: 13/723,923

(22) Filed: Dec. 21, 2012

(65) Prior Publication Data

US 2013/0172595 A1   Jul. 4, 2013

(30) Foreign Application Priority Data

Jan. 3, 2012  (EP) .................................. 12000022

(51) Int. Cl.
*C07F 7/18* (2006.01)

(52) U.S. Cl.
CPC .............. *C07F 7/1876* (2013.01); *C07F 7/1888* (2013.01)
USPC ............ 556/476; 556/452; 556/453; 556/466

(58) Field of Classification Search
USPC .................................. 556/452, 453, 466, 476
See application file for complete search history.

(56) References Cited

U.S. PATENT DOCUMENTS

| 2,731,485 A | 1/1956 | Wagner et al. |
| 4,677,215 A | 6/1987 | Kotzsch et al. |
| 4,958,041 A | 9/1990 | Graefe et al. |
| 6,160,151 A * | 12/2000 | Compton et al. ............ 556/480 |
| 7,459,577 B2 * | 12/2008 | Bannou et al. ............... 556/465 |

OTHER PUBLICATIONS

Extended European Search Report; European Application No. 12000022.9; Date of Mailing: May 9, 2012: 5 Pages.

* cited by examiner

*Primary Examiner* — Sudhakar Katakam
*Assistant Examiner* — Pancham Bakshi
(74) *Attorney, Agent, or Firm* — Cantor Colburn LLP

(57) ABSTRACT

The present invention relates to a method for preparing di-organo-dialkoxysilanes, in particular di-organo-dialkoxysilanes wherein one or both of the organic substituents are bulky. The method comprises reacting a tetraalkoxysilane compound with a first Grignard reagent to form a mono-organo-tri-alkoxysilane compound, which is then reacted with a chlorinating agent to form a chlorinated mono-organo-di-alkoxysilane which is then reacted with a second Grignard reagent to form the di-organo-di-alkoxysilane compound.

19 Claims, No Drawings

METHOD FOR PREPARING DI-ORGANO-DIALKOXYSILANES

CROSS REFERENCE TO RELATED APPLICATIONS

This application claims priority to European Patent Application Serial No. 12000022.9, filed Jan. 3, 2012, the contents of which is herein incorporated by reference in its entirety.

The present invention relates to a method for preparing di-organo-dialkoxysilanes, in particular di-organo-dialkoxysilanes wherein one or both of the organic substituents are bulky.

Di-organo-dialkoxysilanes are included, among other things, as stereo modifiers in catalysts for the production of polypropylenes. Particularly advantageous for that use are disubstituted dialkoxysilanes wherein the organic substituents are branched alkyl chains.

It is well known that di-organodialkoxysilanes can be produced through alkylation or arylation of tetraalkoxysilanes and only occasionally produced by reaction of mono substituted trialkoxysilanes with Grignard reagents (Houben-Weyl, Methods 25 of Organic Chemistry, XIII/5, 180 p).

However, as a rule, the reaction products are produced as mixtures of di-organo-dialkoxysilanes with mono-organo-trialkoxysilanes and/or tri-organo-monoalkoxysilanes, so that the isolation of the desired di-organo-dialkoxysilane requires a separation step.

To that extent U.S. Pat. No. 4,958,041 discloses that certain di-organo-dialkoxysilanes may be readily produced in high yields by reacting mono-organo-trialkoxysilanes or tetraalkoxysilanes with Grignard reagents of general formula RMgX in appropriate solvents. The present inventors have observed that this method only allows certain di-organo-dialkoxysilanes to be produced. In particular the present inventors found that if the Grignard reagent contains rather bulky organic groups and depending on the type of tetraalkoxysilane used the proposed reaction in U.S. Pat. No. 4,958,041 will primarily result in mono-organo-trialkoxysilanes and in no or low amounts in di-organo-dialkoxysilanes. Moreover, this method only allows the preparation of di-organo-dialkoxysilanes wherein the two organic groups are identical.

The observation of the present inventors is supported by the publication "Versatile method for introduction of bulky substituents to alkoxychlorosilanes, Shin Masaoka et al, Journal of Organometallic Chemistry 691 (2006), 182-192" which discloses in example 3.1.21 a reaction of tetra-n-butoxysilane with isopropylmagnesiumchloride to form isopropyl-tri(n-butoxy)silane as the major reaction product.

An object of the present invention is therefore to provide a method to prepare di-organo-dialkoxysilanes wherein one or preferably both of the organic substituents are bulky, using readily available raw materials, with a relatively simple process, at moderate reaction conditions and resulting in relatively high yields.

A further object of the present invention present invention is to provide a method to prepare di-organo-dialkoxysilanes wherein the organic substituents may be different.

To that extent the present inventors have found a method for preparing di-organo-dialkoxysilanes comprising the steps of a) reacting a tetraalkoxysilane compound having the general formula $Si(OR^1)_4$ with a first Grignard reagent of general formula $R^2$—Mg—X, to form a mono-organo-tri-alkoxysilane compound of general formula $R^2$—Si(—$OR^1$)$_3$, wherein the molar ratio of the first Grignard compound and the tetraalkoxysilane compound is from 1 to 1.5;

b) reacting the mono-organo-tri-alkoxysilane compound of step a) with a chlorinating agent to form a chlorinated mono-organo-di-alkoxysilane compound of general formula,

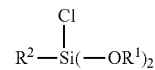

wherein the molar ratio between the mono-organo-tri-alkoxysilane compound to the chlorinating agent is from 1 to 1.5;

c) reacting the chlorinated mono-organo-di-alkoxysilane compound of step b) with a second Grignard reagent of general formula $R^3$—Mg—X to form the di-organo-di-alkoxysilane compound of general formula,

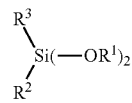

wherein molar ratio of the second Grignard compound and the chlorinated mono-substituted dialkoxy silane compound is from 1 to 1.5; and wherein $R^1$, $R^2$ and $R^3$ are independently selected from the group comprising an alkyl group having 1 to 20 carbon atoms and a cycloalkyl group having 3 to 20 carbon atoms, optionally containing a heteroatom; and X is iodine, bromine or chlorine.

The present inventors have found that for formation of predominantly a mono-organo-trialkoxysilane compound in step a), $R^1$ and/or $R^2$ have to be of a certain bulkiness, i.e. they have to bring about a certain steric hindrance effect during the reaction. Without willing to be being bound to it, the present inventors believe that this bulkiness steric hindrance during the reaction of step a) will prevent or at least significantly limit the formation of di-organo-dialkoxysilane compounds. The term "predominantly" as used herein is to be understood as meaning that the yield of formation of the mono-organo-trialkoxysilane compound is at least 75% of the theoretical maximum yield based on the amount of tetraalkoxysilane compound. Further factors attributing to the formation of predominantly a mono-organo-trialkoxysilane in step a) can be the molar ratio of the first Grignard reagent and the tetraalkoxysilane and/or the reaction conditions, in particular reaction temperature. The skilled person will understand that the amount of steric hindrance as a result of the selection of $R^1$ and $R^2$ will determine the importance of these further factors. For example, selecting a molar ratio of the first Grignard reagent and the tetraalkoxysilane of below 1.5, preferably below 1.2 will reduce the possibility of formation of di-organo-dialkoxysilane compounds in case the steric hindrance is not strong enough to fully prevent formation of such compounds. However, this molar ratio will become less important if the steric hindrance by itself is already so strong that it does not allow formation of di-organo-dialkoxysilane compounds.

Preferably $R^1$ and $R^2$ and/or the reaction conditions are selected such that the yield of the product obtained in step s) is at least 85%.

In order to prepare a di-organo-dialkoxysilane compound, step a) is followed by a step b), wherein one alkoxy group is replaced by a chlorine atom, after which in step c) a second Grignard reaction is carried out to replace this chlorine atom with an organic group $R^3$. This organic group $R^3$ may be the same or different as $R^2$ hence allows preparation of a wide variety of bulky substituted dialkoxysilanes, i.e. a wide variety of di-organo-dialkoxysilanes.

An advantage of the present invention is that it allows the use of readily available and low cost raw materials such as tetramethoxysilane and tetraethoxysilane. Further advantages of the present invention are that the yield of the reaction is relatively high and that the preparation can be carried out at moderate reaction conditions.

$R^1$, $R^2$ and $R^3$ are independently selected from the group comprising an alkyl group having 1 to 20 carbon atoms and a cycloalkyl group having 3 to 20 carbon atoms, optionally containing a heteroatom.

Preferably, at least one of $R^1$, $R^2$ and $R^3$ is a branched alkyl group having 3 to 20 carbon atoms at a secondary or a tertiary carbon situated in α and/or β position to the silicon atom.

Preferably, $R^1$, $R^2$ and $R^3$ are independently selected from the group consisting of an alkyl group having 1 to 20 carbon atoms and a cycloalkyl group having 3 to 20 carbon atoms, optionally containing a heteroatom and at least one of $R^1$, $R^2$ and $R^3$ is a branched alkyl group having 3 to 20 carbon atoms at a secondary or a tertiary carbon situated in α and/or β position to the silicon atom.

Preferably, $R^1$ is a hydrocarbon group having from 1 to 20 carbon atoms, more preferably from 3 to 10 carbon atoms and most preferably from 5 to 10 carbon atoms. $R^1$ can be an alkyl group preferably having from 1 to 10 carbon atoms, and more preferably is selected from a group consisting of methyl, ethyl, n-propyl, iso-propyl, n-butyl, iso-butyl, sec-butyl, n-pentyl, iso-pentyl, n-hexyl, n-heptyl, n-octyl, n-nonyl, n-decyl, preferably ethyl, methyl, n-propyl and iso-propyl. Most preferably, $R^1$ is methyl or ethyl. $R^1$ optionally contains a heteroatom. $R^1$ can be also a cyclic hydrocarbon group with 3 to 10 carbon atoms, such as cyclopentyl, cyclohexyl, or a benzyl group. $R^1$ may also be an alkyl or cycloalkyl group containing a hydrocarbon ring having from 5 to 8 carbon atoms. Preferably $R^1$ does not contain a heteroatom.

Preferably, $R^2$ is a tertiary hydrocarbon group, or a cyclic hydrocarbon group preferably having a ring from 5 to 20 carbon atoms or an alkyl group containing a hydrocarbon ring having from 5 to 20 carbon atoms, with the proviso that if $R^1$ is methyl the cyclic hydrocarbon has a ring from 6 to 20 carbon atoms. The present inventors have found that if $R^1$ is selected to be methyl, the steric hindrance obtained by a cyclic $R^2$ group having less than 6 carbon atoms possibly results in more formation of reaction products other than the desired a mono-organo-tri-alkoxysilane compound, i.e. a yield of formation of the mono-organo-trialkoxysilane compound less than 75%. As a result a step of separation is needed to obtain the desired mono-organo-tri-alkoxysilane compound. More preferably, $R^2$ is selected from the group consisting of cyclic hydrocarbons having a ring of 5 or 6 carbon atoms and tertiary hydrocarbons having from 3 to 10 carbon atoms.

Suitable examples of $R^2$ groups include ethyl, n-propyl, iso-propyl, n-butyl, iso-butyl, sec-butyl, tert-butyl, n-pentyl, iso-pentyl, sec-pentyl, tert-pentyl, n-hexyl, n-heptyl, cyclopentyl, cyclohexyl, cycloheptyl, cyclooctyl, cyclononyl, cyclodecyl, benzyl. Examples of $R^2$ groups being alkyl groups containing a ring are 1-methyl-cyclohexyl, 1-ethyl-cyclohexyl and the like. Cyclic hydrocarbons may also contain branches. $R^2$ optionally contains a heteroatom. Preferably $R^2$ does not contain a heteroatom.

$R^1$ may be the same or different than $R^2$. Preferably $R^1$ is different than $R^2$.

$R^3$ may be a hydrocarbon compound having from 3 to 20 carbon atoms optionally containing a hetero atom. Preferably $R^3$ does not contain a heteroatom.

$R^3$ is preferably selected from the group consisting of cyclic hydrocarbons having a ring of from 5 to 10 carbon atoms, secondary hydrocarbon groups having from 3 to 10 carbon atoms and tertiary hydrocarbon groups having from 3 to 10 carbon atoms. $R^3$ may further be an alkyl group containing a ring (cyclic hydrocarbon group), or $R^3$ may be a cyclic hydrocarbon compound. Examples of $R^3$ are n-propyl, iso-propyl, n-butyl, iso-butyl, sec-butyl, tert-butyl, n-pentyl, iso-pentyl, sec-pentyl, tert-pentyl, n-hexyl, n-heptyl, cyclopentyl, cyclohexyl, cycloheptyl, cyclooctyl, cyclononyl, cyclodecyl, benzyl, 1-methyl-cyclohexyl, 1-ethyl-cyclohexyl, propyl cyclopentyl, cyclopentyl, cyclohexyl, cycloheptyl, cyclooctyl, cyclononyl, cyclodecyl, iso-propyl, sec-butyl, tert-butyl, 1,1-dimethylpropyl, 1-methyl-1-ethylpropyl, 1,1-diethylpropyl, 1,1,2-trimethylpropyl.

$R^3$ may be the same or different than $R^2$, preferably $R^3$ is different than $R^2$.

In a preferred embodiment, $R^1$ is a hydrocarbon group, preferably an alkyl group having from 1 to 10 carbon atoms or a cyclic hydrocarbon group having from 3 to 10 carbon atoms, $R^2$ is a secondary or more preferably tertiary hydrocarbon group or a cyclic hydrocarbon group preferably having a ring of from 5 to 20 carbon atoms, with the proviso that if $R^1$ is methyl the cyclic hydrocarbon has a ring of from 6 to 20 carbon atoms.

The chlorinating agent used in the method of the present invention may be any compound capable of chlorinating the mono-organo-tri-alkoxysilane compound of step a). Particularly suitable for the method of the present invention are inorganic chlorinating agent, such as HCl, $AlCl_3$, $SOCl_2$, $PCl_5$ and $PCl_3$ and $ZnCl_2$, most preferred being HCl and $SOCl_2$ in view of their availability and reactivity.

The Grignard reagents used in the present invention are typically known in the art and may be made in any manner known to the skilled person, such as for instance as described in Grignard Reagents New developments by H. G. Richey 2000 (ISBN 0471999083).

Step a)

The temperature in step a) may be kept between 0° and 25° C., preferably between 5 and 10° C. The reaction may be kept in between this range until the reaction of step a) is completed (as monitored by Gas Chromatography), which means until at least 85% or preferably at least 95% of the tetraalkoxysilane compound has reacted. At lower temperatures the reaction rate becomes undesirably low; whereas higher temperatures may yield more by-products, i.e. decrease the yield of the reaction.

The reaction mixture may be kept at the reaction temperature for a certain amount of time, for example between from 1 to 10 hours, preferably between 3 to 8 hours, to further complete the reaction.

The Grignard reaction of step a) can be carried out in any typically known ether-type solvents, such as for example t-butyl methyl ether and diethyl ether, or in mixed solvent of an ether-type solvent with an aprotic solvent such as hexane, heptane, toluene, and xylene.

The reaction in step a) is normally carried out under inert atmosphere such as for example under nitrogen or argon, because the presence of oxygen in the reaction system brings about a reaction with the Grignard reagent thus resulting in lowering of the yield.

After completion of the reaction of step a), an appropriate amount of a saturated aqueous ammonium chloride solution or a dilute sulfuric acid can be added to dissolve magnesium salt. The amount of the saturated aqueous ammonium chloride solution or a dilute sulfuric acid depends on the amount of the tetraalkoxysilane. For instance, about 10 to 15 ml saturated solution of ammonium chloride may be added for 10 g of tetraalkoxysilane. The organic layer is then typically separated from the aqueous layer. The organic layer so separated may be purified by any method known in the art, for instance by fractional distillation under atmospheric or reduced pressure, whereby there can be recovered a fraction consisting of the desired reaction product, which is the monoalkoxysilane.

Depending on the steric effect that the combination of selected groups $R^1$ and $R^2$ has, the molar ratio of the first Grignard compound and the tetraalkoxysilane compound may have to be from 1 to 1.5, preferably from 1 to 1.2 and more preferably between 1 to 1.1, so as to prevent undesirable formation of di-organo-dialkoxysilane compound. In case the ratio is below 1, the tetraalkoxysilane remains unreacted; whereas higher ratios yield more by-products i.e. and decrease the yield of the reaction.

The materials used in step a) may be added in any order and mixed in any manner known in the art.

The tetraalkoxysilane in step a) may be a single tetraalkoxysilane compound or a mixture of different tetraalkoxysilane compounds, preferably a single tetraalkoxysilane compound. Likewise, the first Grignard reagent in step a) may be a single first Grignard reagent or a mixture of different first Grignard reagents, preferably a single first Grignard reagent.

Step b)

During step b), the reaction temperature may be kept at moderate temperatures, for example a temperature in the range from 10° C. to 50° C., preferably at room temperature, such as between 15 and 30° C. By applying a temperature outside these ranges would decrease the reaction yield. By means of any separation method known in the art, for example by distillation, particularly by vacuum distillation, the chlorinated mono-organo-di-alkoxysilane compound can be obtained.

The materials used in step b) may be added in any order and mixed in any manner known in the art. Preferably, the chlorinated agent may be added gradually to the mono-organo-tri-alkoxysilane, in a certain period of time, such as within maximum 1 hour.

The amount of the chlorinating agent is preferably equivalent to the amount of mono-organo-trialkoxysilane compound, yet the molar ratio between the mono-organo-trialkoxysilane compound to the chlorinating agent may range from 1 to 1.5, preferably from 1 to 1.2, more preferably from 1 to 1.1. In case the ratio is below 1, the mono-organo-trialkoxysilane remains unreacted; whereas higher ratios yield more by-products i.e. and decrease the yield of the reaction.

The obtained reaction product in step b) may be then purified by any means known in the art, preferably by means of distillation.

The chlorinating agent may be a single chlorinating agent or a mixture of different chlorinating agents. Preferred it is a single chlorinating agent.

Step c)

The temperature in step c) may be kept between 0° and 25° C., preferably between 5 and 10° C. The reaction may be kept in between this range until the reaction of step c) is completed (as monitored by Gas Chromatography), which means until at least 95% of mono-organo-di-alkoxysilane compound has reacted. At lower temperatures the reaction rate becomes undesirably low; whereas higher temperatures may yield more by-products, i.e. decrease the yield of the reaction.

The reaction mixture may be kept at the reaction temperature for a certain amount of time, for example between from 1 to 10 hours, preferably between 3 to 8 hours, to complete the reaction.

The Grignard reaction of step c) can be carried out in any typically known ether-type solvents, such as for example t-butyl methyl ether and diethyl ether, or in mixed solvent of an ether-type solvent with an aprotic solvent such as hexane, heptane, toluene, and xylene.

The reaction in step c) is normally carried out under inert atmosphere such as for example under nitrogen or argon, because the presence of oxygen in the reaction system brings about a reaction with the Grignard reagent thus resulting in lowering of the yield.

After completion of the reaction of step c), an appropriate amount of a saturated aqueous ammonium chloride solution or a dilute sulfuric acid can be added to dissolve magnesium salt. The amount of the saturated aqueous ammonium chloride solution or a dilute sulfuric acid typically depends on the amount of the mono-organo-di-alkoxysilane. For instance, about 10 to 15 ml saturated solution of ammonium chloride may be added for 14 g of mono-organo-di-alkoxysilane. The organic layer is then typically separated from the aqueous layer. The organic layer so separated may be purified by any method known in the art, for instance by fractional distillation under atmospheric or reduced pressure, whereby there can be recovered a fraction consisting of the desired reaction product, which is the di-organo-di-alkoxysilane compound.

The molar ratio of the second Grignard compound and the chlorinated mono-substituted dialkoxy silane compound is from 1 to 1.5 preferably from 1 to 1.2, most preferably from 1 to 1.1. In case the ratio is below 1, the chlorinated mono-substituted dialkoxy silane remains unreacted; whereas higher ratios yield more by-products i.e. and decrease the yield of the reaction.

The second Grignard reagent in step c) may be a single second Grignard reagent or a mixture of different second Grignard reagents; preferably a single second Grignard reagent.

The materials used in step c) may be added in any order and mixed in any manner known in the art. Preferably, the second Grignard reagent is prepared separately and afterwards added to the chlorinated mono-substituted dialkoxy silane. After this, the mixture may be kept at reflux temperature (typically determined by the boiling point of the solvent) until reaction is completed, generally between 1 and 6 hours, preferably between 3-6 hours.

The method according to the present invention will now be further explained by means of two non-limiting examples.

EXAMPLE 1

Preparation of Cyclopentyl Isobutyl Diethoxysilane
(e)

The overall reaction scheme for preparing cyclopentyl isobutyl diethoxysilane is as follows:

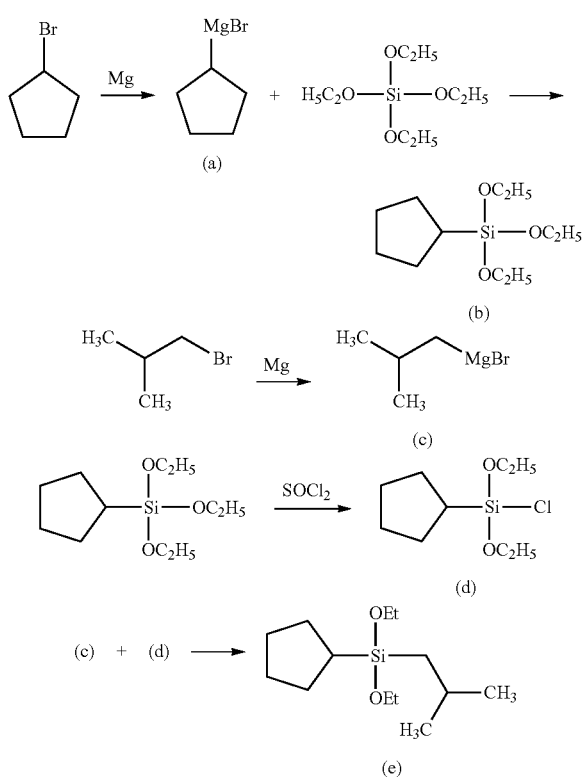

(a) Preparation of Cyclopentyl Magnesium Bromide (1st Grignard Reagent)

1.8 gram (0.074 mole) of metallic magnesium and 25 ml of t-butyl methyl ether were charged in a 250 ml flask equipped with a reflux condenser, dropping funnel and stirring apparatus, in an atmosphere of nitrogen. After stirring was started, iodine crystal and a solution having cyclopentylbromide 10.0 gram (0.067 mole) and 0.2 gram of 1,2-dibromoethane diluted with 25 ml of t-butyl methyl ether was drop wise added from the dropping funnel over a period of 6 hours under reflux of t-butyl methyl ether. After addition the stirring was carried out for 4 hours under reflux to obtain an ether solution of cyclopentyl magnesium bromide.

(b) Preparation of Cyclopentyltriethoxysilane 60 ml of dry t-butyl methyl ether and 14.0 gram (0.067 mole) of tetraethoxysilane were charged in a 250 ml flask equipped with a reflux condenser and a stirring apparatus in an atmosphere of nitrogen and the solution of cyclopentyl magnesium bromide prepared above under (a) was slowly added while keeping the internal temperature below 10° C. After completion of addition stirring was carried out at room temperature for 6 hours and at reflux temperature for 2 hours. To the resulting reaction mass 10-20 ml of saturated aqueous ammonium chloride solution was added drop wise to dissolve magnesium salt. The organic layer was separated from the aqueous layer, dried and evaporated to give crude cyclopentyltriethoxysilane. The crude was purified by fractional distillation under reduced pressure, yielding 12 gram of pure cyclopentyltriethoxysilane (76% of the theoretical maximum yield based on the amount of tetraethoxysilane).

(c) Preparation of Isobutyl Magnesium Bromide (2nd Grignard Reagent)

1.8 gram (0.074 mole) of magnesium and 25 ml of diethyl ether were charged in a 250 ml flask equipped with a reflux condenser, dropping funnel and stirring apparatus, in an atmosphere of nitrogen. After stirring was started, iodine crystal and a solution having Isobutylbromide 9.3 gram (0.067 mole) and 0.2 gram of 1,2-dibromoethane diluted with 25 ml of diethyl diether was drop wise added from the dropping funnel over a period of 2 hours under reflux of diethyl ether. After addition stirring was carried out for 2 hours under reflux to obtain an ether solution of isobutyl magnesium bromide.

(d) Preparation of Chlorocyclopentyldiethoxysilane 5.4 gram of thionyl chloride (0.045 mole) was added drop wise at 25° C. in 1 hour to a stirred mixture of 10.5 gram (0.045 mole) cyclopentyltriethoxysilane (b) and DMF (0.1 ml). The reaction mass was stirred for 4 hours at 25° C. and distilled in vacuum to give chlorocyclopentyldiethoxysilane (d) 8.4 gram (83.8%).

(e) Preparation of Cyclopentyl Isobutyl Diethoxysilane 50 ml of dry diethyl ether and 14.0 gram (0.063 mole) of chlorocyclopentyldiethoxysilane (d) were charged in a 250 ml flask equipped with a reflux condenser and a stirring apparatus in an atmosphere of nitrogen and above prepared solution of isobutyl magnesium bromide was slowly added while keeping the internal temperature below 10° C. After completion of addition stirring was carried out at room temperature for 6 hours and at reflux temperature for 2 hours. To the resulting reaction mass 10-20 ml of saturated aqueous ammonium chloride solution was added drop wise to dissolve magnesium salt. The organic layer was separated from the aqueous phase, dried and evaporated to give crude cyclopentylisobutyldiethoxysilane. This crude was purified by fractional distillation under reduced pressure, yielding 12 gram (78%) of pure cyclopentylisobutyldiethoxysilane.

EXAMPLE 2

Preparation of Cyclohexyl Cyclopentyl Diethoxysilane (e)

The overall reaction scheme for preparing cyclohexyl cyclopentyl diethoxysilane is as follows:

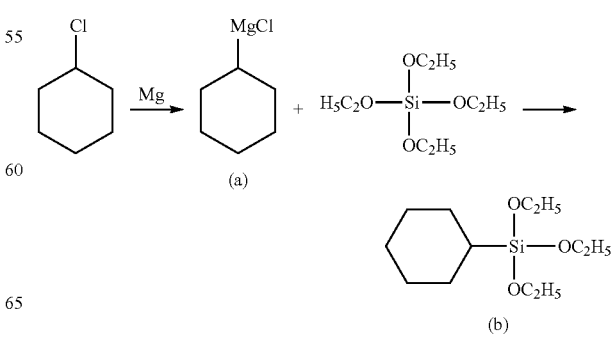

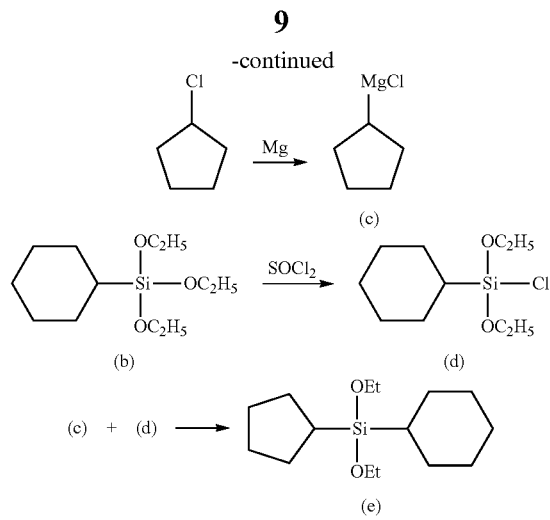

(a) Preparation of Cyclohexyl Magnesium Chloride
(1$^{st}$ Grignard Reagent)

2.18 gram (0.09 mole) of magnesium and 25 ml of diethyl ether were charged in a 250 ml flask equipped with a reflux condenser, dropping funnel and stirring apparatus, in an atmosphere of Nitrogen. After stirring was started, iodine crystal and a solution having cyclohexylchloride 9.5 gram (0.08 mole) and 0.2 gram of 1,2-dibromoethane diluted in 25 ml of diethyl ether was drop wise added from the dropping funnel over a period of 2 hours under reflux of diethyl ether. After addition stirring was carried out for 4 hours under reflux to obtain an ether solution of cyclohexyl magnesium bromide.

(b) Preparation of Cyclohexyltriethoxysilane 60 ml of dry diethyl ether and 14.0 gram (0.067 mole) of tetraethoxysilane were charged in a 250 ml flask equipped with a reflux condenser and a stirring apparatus in an atmosphere of nitrogen and above prepared solution of cyclohexyl magnesium chloride was slowly added while keeping the internal temperature below 10° C. After completion of addition stirring was carried out at room temperature for 6 hours and at reflux temperature for 2 hours. To the resulting reaction mass 10-20 ml of saturated aqueous ammonium chloride solution was added drop wise to dissolve magnesium salt. The organic layer was separated from the aqueous layer, dried and evaporated to give crude cyclohexyltriethoxysilane. This crude was purified by fractional distillation under reduced pressure, yielding 14.2 gram of pure cyclohexyltriethoxysilane (86% of the theoretical maximum yield based on the amount of tetraethoxysilane).

(c) Preparation of Cyclopentyl Magnesium Chloride
(2$^{nd}$ Grignard Reagent)

1.8 gram (0.074 mole) of magnesium and 25 ml of diethyl ether were charged in a 250 ml flask equipped with a reflux condenser, dropping funnel and stirring apparatus, in an atmosphere of nitrogen. After stirring was started, iodine crystal and a solution having cyclopentylchloride 7.6 gram (0.072 mole) and 0.2 gram 1,2-dibromoethane diluted in 25 ml of diethyl diether was drop wise added from the dropping funnel over a period of 2 hours under reflux of diethyl ether. After addition stirring was carried out for 6 hours under reflux to obtain an ether solution of cyclopentyl magnesium chloride (c).

(d) Preparation of Chlorocyclohexyldiethoxysilane 11.6 gram (0.0975 mole) of thionyl chloride was added drop wise at 25° C. in 1 hour to a stirred mixture of 20 gram (0.08 mole)cyclohexyltriethoxysilane (b) and DMF (0.1 ml). The reaction mass was stirred for 4 hours at 25° C. and distilled in vacuum to give chlorocyclohexyldiethoxysilane (d) 15.4 gram (81%).

(e) Preparation of Cyclopentylcyclohexyldiethoxysilane 60 ml of dry diethyl ether and 14.0 gram (0.063 mole) of chlorocyclohexyldiethoxysilane (d) were charged in a 250 ml flask equipped with a reflux condenser and a stirring apparatus in an atmosphere of nitrogen and the above prepared solution of cyclopentyl magnesium chloride (2$^{nd}$ Grignard reagent) was slowly added while keeping the internal temperature below 10° C. After completion of addition stirring was carried out at room temperature for 6 hours and at reflux temperature for 5 hours. To the resulting reaction mass 10-20 ml of saturated aqueous ammonium chloride solution was added drop wise to dissolve magnesium salt. The organic layer was separated from the aqueous phase, dried and evaporated to give crude cyclopentylisobutyldiethoxysilane. This crude was purified by fractional distillation under reduced pressure, yielding 12 gram (75%) of pure cyclopentylisobutyldiethoxysilane.

The invention claimed is:
1. A method for preparing a di-organo-di-alkoxysilane compound comprising:
   a) reacting a tetraalkoxysilane compound having the general formula Si(OR$^1$)$_4$ with a first Grignard reagent of general formula R$^2$—Mg—X, to form a mono-organo-tri-alkoxysilane compound of general formula R$^2$—Si(—OR$^1$)$_3$, wherein a molar ratio of the first Grignard compound and the tetraalkoxysilane compound is from 1 to 1.5;
   b) reacting the mono-organo-tri-alkoxysilane compound of step a) with a chlorinating agent to form a chlorinated mono-organo-di-alkoxysilane compound of general formula,

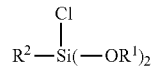

wherein a molar ratio between the mono-organo-tri-alkoxysilane compound to the chlorinating agent is from 1 to 1.5;
   c) reacting the chlorinated mono-organo-di-alkoxysilane compound of step b) with a second Grignard reagent of general formula R$^3$—Mg—X to form the di-organo-di-alkoxysilane compound of general formula,

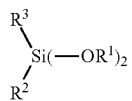

wherein a molar ratio of the second Grignard compound and the chlorinated mono-substituted dialkoxy silane compound is from 1 to 1.5; and wherein $R^1$, $R^2$ and $R^3$ are independently selected from an alkyl group having 1 to 20 carbon atoms, and a cycloalkyl group having 3 to 20 carbon atoms, optionally containing a heteroatom; and wherein X is iodine, bromine or chlorine.

2. The method according to claim 1, wherein at least one of $R^1$, $R^2$ and $R^3$ is a branched alkyl group having 3 to 20 carbon atoms at a secondary or a tertiary carbon situated in α and/or β position to the silicon atom.

3. The method according to claim 1, wherein the chlorinating agent is selected from HCl, $AlCl_3$, $SOCl_2$, $PCl_5$, $PCl_3$, and $ZnCl_2$.

4. The method according to claim 1, wherein the chlorinating agent is selected from HCl and $SOCl_2$.

5. The method according to claim 1, wherein the reaction temperature in step a) is kept between 0 and 25° C.

6. The method according to claim 1, wherein in step a) a molar ratio of the first Grignard compound and the tetraalkoxysilane compound is from 1 to 1.2.

7. The method according to claim 1, wherein in step b) a molar ratio of the mono-organo-tri-alkoxysilane compound and the chlorinating agent is from 1 to 1.2.

8. The method according to claim 7, wherein in step b) a molar ratio of the mono-organo-tri-alkoxysilane compound and the chlorinating agent is from 1 to 1.1.

9. The method according to claim 1, wherein in step c) a molar ratio of the second Grignard compound and the chlorinated mono-substituted dialkoxy silane compound is from 1 to 1.2.

10. The method according to claim 1, wherein $R^1$ is an alkyl group having from one to ten carbon atoms.

11. The method according to claim 10, wherein $R^1$ is selected from methyl, ethyl, n-propyl, iso-propyl, n-butyl, iso-butyl, sec-butyl, n-pentyl, iso-pentyl, n-hexyl, n-heptyl, n-octyl, n-nonyl, and n-decyl.

12. The method according to claim 11, wherein $R^1$ is selected from ethyl, methyl, n-propyl and iso-propyl.

13. The method according to claim 1, wherein $R^2$ is a secondary or a tertiary alkyl group or a cycloalkyl group, with the proviso that if $R^1$ is methyl the cycloalkyl group has a ring of from 6 to 20 carbon atoms.

14. The method according to claim 13, wherein $R^2$ is a secondary or a tertiary alkyl group or a cycloalkyl group having a ring of from 5 to 20 carbon atoms.

15. The method according to claim 13, wherein $R^1$ is a hydrocarbon group having from 1 to 10 carbon atoms and $R^3$ is different from $R^2$.

16. The method according to claim 13, wherein $R^2$ is selected from cyclic hydrocarbons having a ring of 5 or 6 carbon atoms and tertiary hydrocarbons having from 3 to 10 carbon atoms.

17. The method according to claim 1, wherein $R^3$ is a hydrocarbon compound having from 3 to 20 carbon atoms optionally containing a hetero atom.

18. The method according to claim 1, wherein $R^3$ is selected from cyclic hydrocarbons having a ring of from 5 to 10 carbon atoms, secondary hydrocarbon groups having from 3 to 10 carbon atoms, and tertiary hydrocarbon groups having from 3 to 10 carbon atoms.

19. A method for preparing a di-organo-di-alkoxysilane compound comprising:

a) reacting a tetraalkoxysilane compound having the general formula $Si(OR^1)_4$ with a first Grignard reagent of general formula $R^2$—Mg—X, to form a mono-organo-tri-alkoxysilane compound of general formula $R^2$—Si(—$OR^1)_3$, wherein a molar ratio of the first Grignard compound and the tetraalkoxysilane compound is from 1 to 1.5;

b) reacting the mono-organo-tri-alkoxysilane compound of step a) with a chlorinating agent to form a chlorinated mono-organo-di-alkoxysilane compound of general formula,

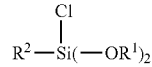

wherein a molar ratio between the mono-organo-tri-alkoxysilane compound to the chlorinating agent is from 1 to 1.5;

c) reacting the chlorinated mono-organo-di-alkoxysilane compound of step b) with a second Grignard reagent of general formula $R^3$—Mg—X to form the di-organo-di-alkoxysilane compound of general formula,

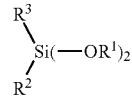

wherein a molar ratio of the second Grignard compound and the chlorinated mono-substituted dialkoxy silane compound is from 1 to 1.5; and wherein $R^1$ is a hydrocarbon group having from 1 to 20 carbon atoms; $R^2$ is a tertiary hydrocarbon group, a cyclic hydrocarbon group having a ring from 5 to 20 carbon atoms, or an alkyl group containing a hydrocarbon ring having from 5 to 20 carbon atoms with the proviso that if $R^1$ is methyl the hydrocarbon ring has 6 to 20 carbon atoms; and $R^3$ is a hydrocarbon group having 3 to 20 carbon atoms; wherein one or more of $R^1$, $R^2$, and $R^3$ optionally contains a heteroatom; wherein X is iodine, bromine, or chlorine.

* * * * *